(12) United States Patent  
Oyamada et al.

(10) Patent No.: US 8,043,866 B2  
(45) Date of Patent: Oct. 25, 2011

(54) IMMUNOCHROMATOGRAPHY METHOD

(75) Inventors: Takayoshi Oyamada, Kanagawa (JP); Junichi Katada, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 137 days.

(21) Appl. No.: 12/285,119

(22) Filed: Sep. 29, 2008

(65) Prior Publication Data

US 2009/0111196 A1   Apr. 30, 2009

(30) Foreign Application Priority Data

Sep. 28, 2007   (JP) ................. 2007-254176

(51) Int. Cl.
*G01N 33/53* (2006.01)

(52) U.S. Cl. ............. 436/514; 435/7.1; 435/4; 435/810; 530/414; 530/415; 530/416; 530/424; 436/518; 436/808; 436/80; 436/970

(58) Field of Classification Search .................. 435/7.1, 435/4, 810; 430/414, 415, 416, 424, 477, 430/479, 480, 542; 436/514, 518, 73, 80, 436/808, 810, 970

See application file for complete search history.

(56) References Cited

U.S. PATENT DOCUMENTS

| | | | |
|---|---|---|---|
| 5,206,122 A * | 4/1993 | Noppe et al. | 430/414 |
| 6,146,589 A | 11/2000 | Chandler | |
| 2007/0128679 A1 * | 6/2007 | Lelental et al. | 435/7.92 |

FOREIGN PATENT DOCUMENTS

| | | |
|---|---|---|
| JP | 10-513263 A | 12/1998 |
| JP | 2002-202307 A | 7/2002 |
| WO | WO-96/24060 A1 | 8/1996 |

* cited by examiner

*Primary Examiner* — Bao Thuy L Nguyen  
(74) *Attorney, Agent, or Firm* — Birch, Stewart, Kolasch & Birch, LLP

(57) ABSTRACT

A object of the present invention is to provide an immunochromatography method that makes it possible to rapidly detect an ultratrace amount of an analyte that has been impossible to analyze by conventional immunochromatography methods. The present invention provides an immunochromatography method, which comprises developing an analyte and a labeling substance which is modified with a first binding substance against the analyte in a mixed state on a porous carrier and capturing the analyte and the label at a reaction site on the porous carrier having a second binding substance against the analyte or a substance capable of binding to the first binding substance against the analyte, so as to detect the analyte, wherein the labeling substance having an average particle size of 1 μm or more and 20 μm or less is detected.

6 Claims, 2 Drawing Sheets

IMMUNOCHROMATOGRAPHY METHOD

This application claims priority under 35 U.S.C. §119(a)-(d) on Patent Application No. 2007-254176 filed in Japan on Sep. 28, 2007, the entire contents of which are hereby incorporated by reference.

TECHNICAL FIELD

The present invention relates to an immunochromatography method, which enables rapid detection of an ultratrace amount of an analyte that has been impossible to analyze by conventional immunochromatography methods, for example by controlling the size of the label at the time of detection via amplification of the signal of a label.

BACKGROUND ART

Among bioactive substances or environmental pollutants such as natural products, toxins, hormones, or agricultural chemicals, numerous substances act in ultratrace amounts. Accordingly, instrumental analytical methods capable of performing high-sensitivity analysis have conventionally been widely used for qualitative and quantitative measurement of these substances. However, instrumental analytical methods are poor in specificity, require excessive time for analysis including pretreatment of samples, and are troublesome in operation. Thus instrumental analytical methods are inconvenient for the purpose of rapid and convenient measurements that have been required in recent years. Meanwhile, immunoassays are highly specific and much easier in terms of operation than instrumental analytical methods. Therefore immunoassays have gradually spread in the field of measurement of bioactive substances and environmental pollutants. However, conventional immunoassays such as enzyme immunoassays using 96-well plates and latex agglutination assays do not always provide satisfactory rapidness and convenience for measurement or detection sensitivity.

Another need expected to be enabled is as follows. Achievement of higher sensitivity of tests that currently use relatively invasive samples such as swabs and blood makes it possible to detect very small amounts of analytes contained in relatively low-invasive samples such as snot, mouth wash, and urine. Thus, less burdensome tests of patients can be realized.

In recent years, test kits using an immunochromatography method (hereinafter referred to as an immunochromatography kit) have been used more often in examination of infections that require particularly rapid diagnosis. According to the spread of these kits, patients with infections can be identified by a rapid and convenient method, and subsequent diagnosis and therapy can be conducted immediately and accurately. For example, in an immunochromatography method using the sandwich method, a labeled second antibody capable of specifically binding to an analyte (for example, an antigen), and a sample solution which may possibly contain the analyte are developed on an insoluble thin film-shaped support (for example, a glass fiber membrane, a nylon membrane, or a cellulose membrane) on which a first antibody capable of specifically binding to the analyte has been immobilized in a specific region. As a result, an immune complex with the analyte is formed at the region of the insoluble thin film-shaped carrier, on which region the first antibody has been immobilized. The analyte can be measured by detecting a signal such as color development or coloring of a label. The label to be used herein may be, for example, a protein such as an enzyme, colored latex particles, metal colloids, or carbon particles.

The immunochromatography method requires neither massive facilities nor instruments for determination and measurement. Furthermore, the immunochromatography method is simple in operation and promptly gives measurement results by introducing a sample solution dropwise which may possibly contain an analyte and leaving it for approximately 5 to 10 minutes. For this reason, this technique is used widely as a convenient, rapid, and highly specific method for determination and measurement in many scenarios, such as for clinical examination in hospitals and in assays in laboratories.

Among bioactive substances or environmental pollutants such as natural products, toxins, hormones, and agricultural chemicals, and specimens of early infection stage of virus disease, many substances exert effects in ultratrace amounts that are undetectable by conventional common immunochromatography methods. Therefore, there are demands for development of rapid, convenient, and highly sensitive immunochromatography methods for such substances.

JP Patent Publication (Kokai) No. 2002-202307 A discloses that gold colloids were amplified using a silver sensitizer, "Silver Enhancing Kit (Cat. SEKB250); produced by British BioCell International." However, the relevant method requires 10 or more minutes for amplification, lacking the rapidness that is a characteristic of immunochromatography methods. Furthermore, JP Patent Publication (Kohyo) No. 10-513263 A (1998) discloses that gold colloids are amplified using an optical microscope silver enhancing kit (SELK15; produced by British BioCell International). Since the amount of labeling substance at detection site can not be specified by the disclosure of JP Patent Publication (Kohyo) No. 10-513263 A (1998), a makeup experiment was carried out using an amplification kit for photomicroscope, SEKL15 (British Biocell International), wherein the amount of the labeling substance at the detection site was changed. As a result, although amplification was confirmed, the particle size was only 350 nm. From this result, it was considered that a particle of 1 nm which cannot be observed visually is amplified and very small amount of analyte cannot be detected in JP Patent Publication (Kohyo) No. 10-513263 A (1998).

DISCLOSURE OF THE INVENTION

Regarding immunochromatography methods using a gold colloid as a label, a silver amplification method is known as a method for increasing sensitivity. However, it has been impossible to realize amplification of extremely fine amounts ($10^6/mm^3$ or less) of a label within 10 minutes in a way that has practical meaning. Specifically, an object to be achieved by the present invention is to provide an immunochromatography method that makes it possible to rapidly detect an ultratrace amount of an analyte that has been impossible to analyze by conventional immunochromatography methods.

In the present invention, it has been discovered that when the average particle size of a label at the time of detection is 1 µm or more and 20 µm or less, detection is possible even with an extremely few number of the label (e.g., $10^6/mm3$ or less). Moreover, such size is required only when detection is performed in the present invention. Thus, it has been discovered that amplification of the size of a label within 7 minutes or less and the control of the average particle size to be 1 µm or more and 20 µm or less are more important. The reason is as follows: if the size of the label is 1 µm or more from the time of the initiation of analysis in an immunochromatography method, non-specific absorption tends to occur due to its size when the label moves in the membrane at the time of analysis, and such non-specific adsorption causes decrease of detection sensitivity, rather than increase of detection sensitivity.

In addition, the same size or a smaller size than the size range of the present invention is problematic, such that the resulting detection ability is poor when the number of a label is extremely low ($10^6/mm^3$ or less). Furthermore, the same size or a larger size than the size range of the present invention is also problematic, such that many of the results are false-positive. If the size of label is 20 μm or more, false positive results will be increased. The reasons is as follows: If the size of label is 20 μm or more, even very small amount ($10/mm^3$) of label can be observed visually, and thus there is almost no difference a specific adsorption via test substance and a non-specific adsorption not via test substance at detection line.

The present invention has been completed based on the above findings.

The present invention provides an immunochromatography method, which comprises developing an analyte and a labeling substance which is modified with a first binding substance against the analyte in a mixed state on a porous carrier and capturing the analyte and the label at a reaction site on the porous carrier having a second binding substance against the analyte or a substance capable of binding to the first binding substance against the analyte, so as to detect the analyte, wherein the labeling substance having an average particle size of 1 μm or more and 20 μm or less is detected.

Preferably, the average particle size of the labeling substance at the time of detection is 3 μm or more and 20 μm or less.

A method for controlling the average particle size of the labeling substance at the time of detection within the range defined in the present invention may include the following methods, and the method may be used alone or in combination.

(1) The first means is amplification time. If the amplification time is long, the particle size can be increased.
(2) The second means is the degree of reducing ability of the reducing agent. If the degree of reducing ability of the reducing agent is stronger, the particle size can be increased. On the other hand, if the degree of reducing ability of the reducing agent is too strong, a new particle may be generated at a region other than the label before detection. Therefore, strict control is necessary. For example, it is necessary to control the reducing ability of the reducing agent by controlling the ratio of $Fe^{2+}$ and $Fe^{3+}$.
(3) The third means is the concentration of a substance such as silver ions, which is attached with the label to increase the size. If the concentration of such a substance is higher, the particle size can be increased.
(4) The fourth means is the amplification temperature. An optimized temperature of the amplification temperature is determined based on the type and amount of reducing agent, and the concentration of a substance which is used to increase the size.

It is important to control the average particle size of the labeling substance at the time of detection within 1 μm or more and 20 μm or less by combining the aforementioned means. It is very difficult to control the average particle size of the labeling substance at the time of detection to be 1 μm or more especially in 7 minutes or less. However, in the present invention, amplification is controlled by considering the aforementioned parameters, and the size could be stably increased. Thus, the immunochromatography method of the present invention which can detect trace amount of analyte has been completed.

Preferably, the first binding substance is an antibody, and/or the second binding substance is an antibody.

Preferably, an analyte is detected via sensitization using a silver-containing compound and a reducing agent for silver ions.

Preferably, the reaction time for sensitization using the silver-containing compound and the reducing agent for silver ions is within 7 minutes, more preferably within 5 minutes, and further more preferably within 90 seconds.

Preferably, the number of the labeling substance on the detection site is $1\times10^6/mm^3$ or less, more preferably $1\times10^5/mm^3$ or less, and further more preferably $1\times10^4/mm^3$ or less.

Preferably, the labeling substance is a metal colloid.

Preferably, the labeling substance is a gold colloid, a silver colloid, or a platinum colloid.

Preferably, the reducing agent for silver ions is $Fe^{2+}$.

The present invention makes it possible to detect an ultratrace amount of an analyte that has been impossible to analyze by conventional methods, by determining the size of a label upon detection to be an average particle size of 1 μm or more and 20 μm or less. Moreover, the present invention further makes it possible to realize larger sizes of labels rapidly (for example, within 7 minutes or less).

BEST MODE FOR CARRYING OUT THE INVENTION

1. Immunochromatography

Figure 1:
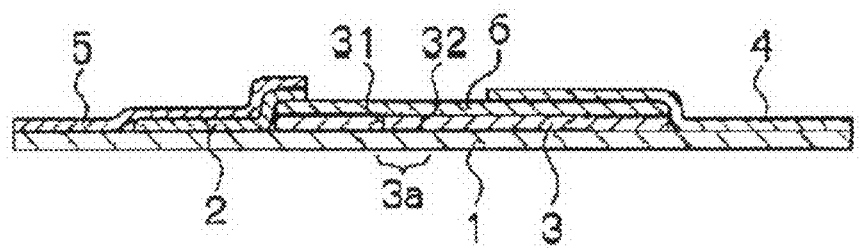
FIG. 1 is a longitudinal sectional view which schematically illustrates a longitudinal sectional view of the immunochromatography kit that can be used in the present invention. 1: Back pressure-sensitive adhesive sheet, 2: Gold colloidal antibody holding pad, 3: Antibody-immobilized membrane, 3a: Capture site, 31: Detection part, 32: Control part, 4: Absorbent pad, 5: Sample addition pad, and 6: Sensitized sheet
Figure 2:
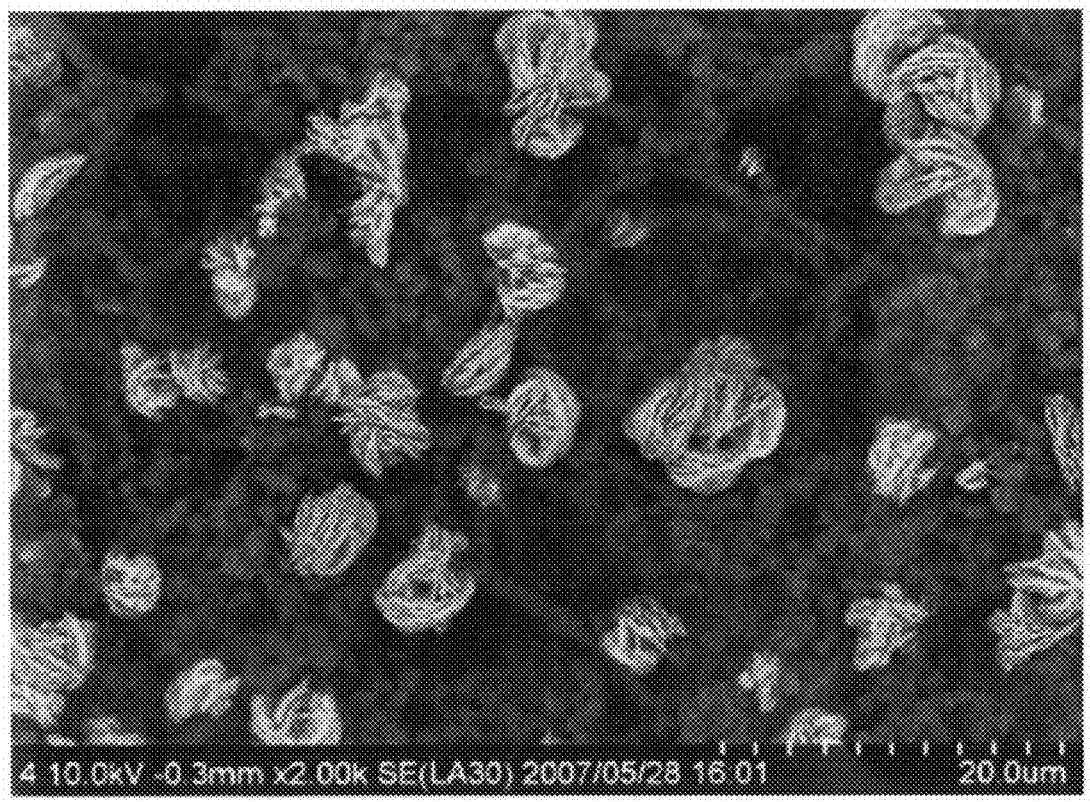
FIG. 2 shows labeling substance when the developing solution A (the present invention) was used.
Figure 3:
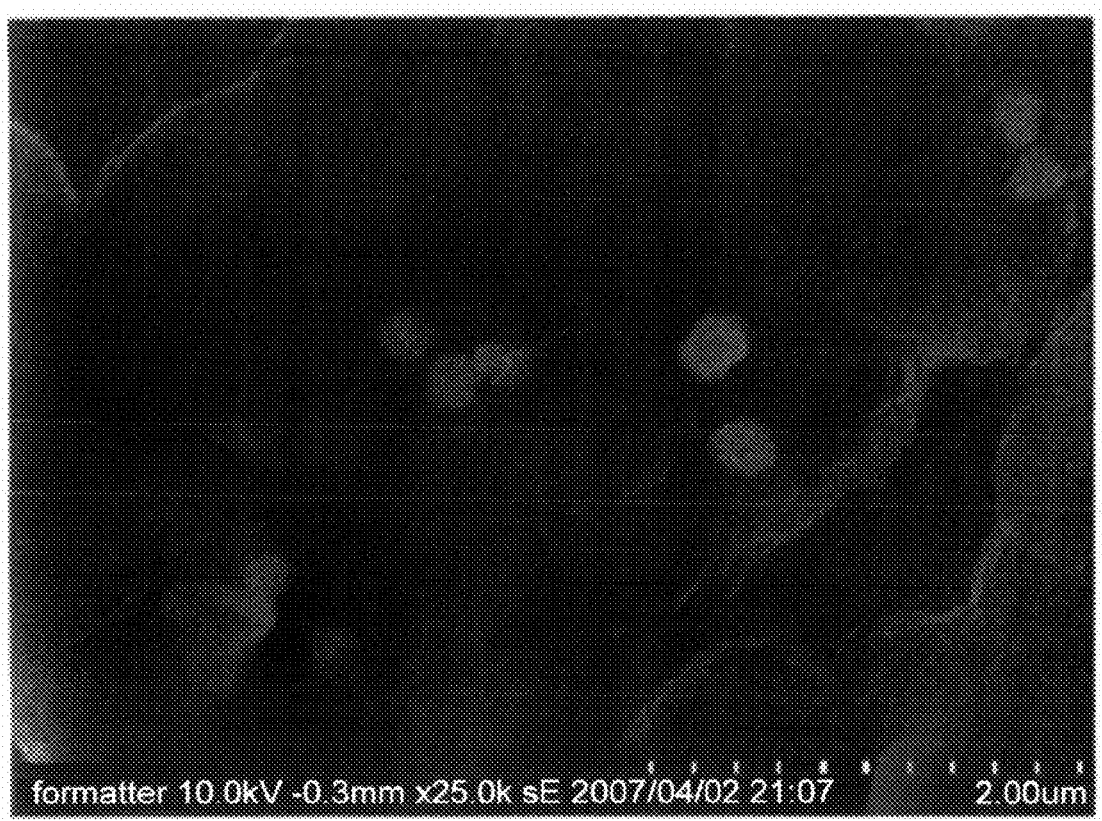
FIG. 3 shows labeling substance when the developing solution H (comparative example) was used.

In general, immunochromatography is a method for determining and/or measuring an analyte, simply, rapidly and specifically, by the following means. That is to say, a chromatographic carrier having at least one reaction site comprising an immobilizing reagent (an antibody, an antigen, etc.) capable of binding to an analyte is used as an immobilization phase. On this chromatographic carrier, a dispersed liquid formed by dispersion of a labeling substance used in detection, which is modified by a reagent capable of binding to an analytical target, is used as a mobile phase, and the mobile phase is moved in the chromatographic carrier in a chromatographic manner. At the same time, the aforementioned analytical target specifically binds to the labeling substance used in detection, and they reach the aforementioned reaction site. At the aforementioned reaction site, a complex of the aforementioned analytical target and the aforementioned labeling substance used in detection specifically binds to the aforementioned immobilizing reagent. Utilizing the phenomenon whereby the labeling substance used in detection is concentrated in the immobilizing reagent portion only when the analytical target exists in an analyzed solution, the presence of a product to be detected in the analyzed solution is qualitatively and quantitatively analyzed by visual observation or using an adequate apparatus.

The apparatus used to perform such an immunochromatography in the present invention may comprise a compound containing silver and a reducing agent for silver ion. A signal is amplified by an amplification reaction using, as a core, a complex of the aforementioned analytical target and the aforementioned labeling substance used in detection binding to the aforementioned immobilizing reagent, so as to achieve high sensitivity. According to the present invention, a rapid and highly sensitive immunochromatography can be carried out.

2. Test Sample

The type of a test sample that can be analyzed by the immunochromatography of the present invention is not particularly limited, as long as it may comprise an analytical target. Examples of such a test sample include biological samples such as the body fluids of animals (particularly, a human) (e.g. blood, serum, plasma, spinal fluid, lacrimal fluid, sweat, urine, pus, runny nose, and sputum), excrements (e.g. feces), organs, tissues, mucous membranes, skin, a swab and a rinsed solution that are considered to contain them, and animals or plants themselves or the dried products thereof.

3. Pre-Treatment of Test Sample

In the immunochromatography of the present invention, the aforementioned test sample can directly be used. Otherwise, the aforementioned test sample can also be used in the form of an extract obtained by extracting it with a suitable extraction solvent, or in the form of a diluted solution obtained by diluting the aforementioned extract using a suitable diluent, or in the form of a concentrate obtained by concentrating the aforementioned extract by a suitable method. As the aforementioned extraction solvent, solvents used in common immunological analysis methods (e.g. water, a normal saline solution, a buffer, etc.) or water-miscible organic solvents that enable a direct antigen-antibody reaction as a result of dilution with the aforementioned solvents can be used.

4. Structure

The type of an immunochromatographic strip that can be used in the immunochromatography of the present invention is not particularly limited, as long as it is an immunochromatographic strip that can be used in a common immunochromatography. For example, FIG. 1 schematically shows a longitudinal section of one example of the immunochromatographic strip of the present invention.

In an immunochromatographic strip of the present invention, a sample-adding pad 5, a labeling substance-retaining pad (e.g. a gold colloid antibody-retaining pad) 2, a chromatographic carrier (e.g. an antibody-immobilized membrane) 3, and an absorbent pad 4 are disposed in this order on an adhesive sheet 5 from the upstream to the downstream of a development direction.

The chromatographic carrier 3 has a capturing site 3a and a detection zone (which is also referred to as a "detection portion") 31 that is a region on which an antibody or an antigen specifically binding to an analytical target is immobilized. The chromatographic carrier 3 also has a control zone (which is also referred to as a "control portion") 32 that is a region on which a control antibody or antigen is immobilized, as desired. Further, the detection zone 31 and the control zone 32 comprise organic silver salts used for amplification and reducing agents used for silver ion.

The labeling substance-retaining pad 2 can be produced by preparing a suspension containing a labeling substance, applying the suspension to a suitable absorbent pad (e.g. a glass fiber pad), and then drying it.

As the sample-adding pad 1, a glass fiber pad can be used, for example.

4-1. Labeling Substance Used in Detection

As a labeling substance used in detection, a color particle used in immune agglutination can be used. For example, metals such as a metal colloid can be used. The mean particle diameter of a carrier particle (or colloid) is preferably between 0.001 and 1 μm. Liposomes or microcapsules containing pigments can also be used as such color particles. Conventionally known color metal colloids can all be used as such color particles for labeling. Examples of such color metal colloids include a gold colloid, a silver colloid, a platinum colloid, an iron colloid, an aluminum hydroxide colloid, and a complex colloid thereof. Preferred examples include a gold colloid, a silver colloid, a platinum colloid, and a complex colloid thereof. A gold colloid and a silver colloid are particularly preferable in that the gold colloid exhibits a red color and the silver colloid exhibits a yellow color when they have an appropriate particle diameter. The mean particle diameter of a metal colloid is preferably between approximately 1 nm and 500 nm, more preferably between 1 nm and 50 nm, and particularly preferably between 1 nm and 15 nm.

Such a metal colloid can be bound to a specifically binding substance according to conventionally known methods (e.g. The Journal of Histochemistry and Cytochemistry, Vol. 30, No. 7, pp. 691-696 (1982)). That is to say, a metal colloid is mixed with a specifically binding substance (e.g. an antibody) in a suitable buffer at room temperature for 5 or more minutes. After completion of the reaction, a precipitate obtained by centrifugation is dispersed in a solution containing a dispersant such as polyethylene glycol to obtain a metal colloid-labeled specifically binding substance of interest. When gold colloid particles are used as the metal colloid, commercially available gold colloid particles may be used. Alternatively, such gold colloid particles may be prepared by a common method, for example, by a method of reducing chlorauric acid with sodium citrate (Nature Phys. Sci., vol. 241, 20 (1973), etc.). The present invention is characterized in that the size of the labeling substance for detection at the time of detection is 1 μm or more and 20 μm or less, and preferably 3 μm or more and 20 μm or less. As a method for changing the size of the substance from the size before detection to the size at the time of detection, an amplification reaction using an a reducing agent can be used.

According to the present invention, in an immunochromatography using, as a labeling substance used in detection, a metal colloid labeling substance, a metallic sulfide labeling substance, a metal alloy labeling substance (hereinafter also referred to as a metallic labeling substance), or a metal-containing polymer particle labeling substance, the signal from the aforementioned metallic labeling substance can be amplified. Specifically, after formation of a complex of the analytical target and the labeling substance used in detection, silver ions supplied from a compound containing silver such as an inorganic silver salt or an organic silver salt are allowed to come into contact with a reducing agent for silver ions, so that the silver ions are reduced with the reducing agent to form silver particles. Thus, the silver particles are deposited on the aforementioned metallic labeling substance as a core, so that the metallic labeling substance is amplified to enable the high-sensitivity analysis of the analytical target. Accordingly, the conventionally known immunochromatography can directly be applied to the immunochromatography of the present invention with the exception that a reaction of precipitating silver particles generated as a result of reduction of silver ions with the reducing agent on the labeling substance of an immune complex is carried out, so as to analyze the thus amplified signal.

In the immunochromatography of the present invention, a metal colloid labeling substance or a metallic sulfide labeling substance may be used as a labeling substance for labeling an antibody or antigen which specifically binds to an analytical target (an antigen or an antibody), or for labeling a standard compound. The type of such a metal colloid labeling substance or a metallic sulfide labeling substance is not particularly limited, as long as it can be used in an ordinary immunochromatography. Examples of such a metal colloid labeling substance include a platinum colloid, a gold colloid, a palladium colloid, a silver colloid, and a mixture thereof. Examples of such a metallic sulfide labeling substance include sulfides of iron, silver, palladium, lead, copper, cadmium, bismuth, antimony, tin, and mercury. In the immunochromatography of the present invention, one or more selected from these metal colloid labeling substances and/or metallic sulfide labeling substances may be used as a labeling substance(s).

4-2. Binding Substance

In the present invention, a labeling substance is modified with a first binding substance reacting with the test substance. The type of the first binding substance reacting with the test substance may be any substance so long as it has an affinity against the test substance. Examples of the first binding substance may include an antibody against the test substance (antigen), an antigen against the test substance (antibody), or an aptamer against the test substance (protein, low molecular weight compound, or the like), but are not limited thereto.

In the present invention, the porous carrier has (a) a second binding substance reacting with the test substance, or (b) a substance binding with the first binding substance. The type of the second binding substance reacting with the test substance may be any substance so long as it has an affinity against the test substance. Examples of the second binding substance may include an antibody against the test substance (antigen), an antigen against the test substance (antibody), or an aptamer against the test substance (protein, low molecular weight compound, or the like), but are not limited thereto. The second binding substance may be the same as or different from the first binding substance. Examples of the substance binding with the first binding substance may be the test substance, or a substance having a site which is recognized by the first binding substance, and may be a substance which is obtained by binding a derivative of the test substance with a protein (for example, BSA).

Preferably, the first binding substance is an antibody, and/or the second binding substance is an antibody. In the immunochromatography of the present invention, the type of an antibody having specificity for an analytical target is not particularly limited. Examples of an antibody used herein include an antiserum prepared from the serum of an animal immunized with the analytical target, an immunoglobulin fraction purified from the antiserum, a monoclonal antibody obtained by cell fusion using the splenic cells of the animal immunized with the analytical target, and the fragments thereof (for example, F(ab')2, Fab, Fab' or Fv). Such an antibody may be prepared by a common method.

4-3. Chromatographic Carrier

The chromatographic carrier is preferably a porous carrier. It is particularly preferably a nitrocellulose membrane, a cellulose membrane, an acetyl cellulose membrane, a polysulfone membrane, a polyether sulfone membrane, a nylon membrane, glass fibers, a nonwoven fabric, a cloth, threads or the like.

Usually, a substance used in detection is immobilized on a part of the chromatographic carrier to form a detection zone. The substance used in detection may be directly immobilized on a part of the chromatographic carrier via a physical or chemical bond. Alternatively, the substance used in detection may be bound physically or chemically to fine particles such as latex particles, and thereafter, the fine particles are immobilized on a part of the chromatographic carrier by trapping them thereon. After immobilization of the substance used in detection on the chromatographic carrier, the chromatographic carrier may preferably be subjected to a treatment for preventing unspecific adsorption, such as a treatment using an inert protein, and it may be then used.

4-4. Sample-Adding Pad

Examples of a material for the sample-adding pad include, but are not limited to, those having uniform characteristics, such as a cellulose filter paper, glass fibers, polyurethane, polyacetate, cellulose acetate, nylon, and a cotton cloth. A sample-adding portion not only acts to receive a sample containing the added analytical target, but also acts to filter off insoluble particles, etc. contained in the sample. Moreover, in order to prevent a decrease in analysis precision occurring during the analysis due to unspecific adsorption of the analytical target contained in the sample on the material of the sample-adding portion, the material constituting the sample-adding portion may be subjected to a treatment for preventing unspecific adsorption before use.

4-5. Labeling Substance-Retaining Pad

Examples of a material for the labeling substance-retaining pad include a cellulose filter paper, glass fibers, and a nonwoven fabric. Such a labeling substance-retaining pad is prepared by impregnating the pad with a predetermined amount of the labeling substance used in detection as prepared above and then drying it.

4-6. Absorbent Pad

The absorbent pad is a portion for physically absorbing the added sample as a result of the chromatographic migration and for absorbing and removing an unreacted labeling substance, etc. that is not immobilized on the detection portion of the chromatographic carrier. Examples of a material for the absorbent pad include water-absorbing materials such as a cellulose filter paper, a nonwoven fabric, a cloth or cellulose acetate. The chromatographic speed after the chromatographic leading end of the added sample has reached the absorbing portion varies depending on the material and size of the absorbent material, etc. Thus, a speed adequate for the measurement of the analytical target can be determined by selection of the material and size of the absorbent material.

5. Immunological Test Method

Hereinafter, a sandwich method and a competitive method, which are specific embodiments of the immunochromatography of the present invention, will be described.

In the sandwich method, an analytical target can be analyzed by the following procedures, for example, but the procedures are not particularly limited thereto. First, a primary antibody and a secondary antibody having specificity for an analytical target (an antigen) have previously been prepared by the aforementioned method. In addition, the primary antibody has previously been labeled. The second antibody is immobilized on a suitable insoluble thin-membrane support (e.g. a nitrocellulose membrane, a glass fiber membrane, a nylon membrane, a cellulose membrane, etc.), and it is then allowed to come into contact with a test sample (or an extract thereof) that is likely to contain the analytical target (the antigen). If the analytical target actually exists in the test sample, an antigen-antibody reaction occurs. This antigen-antibody reaction can be carried out in the same manner as that of an ordinary antigen-antibody reaction. At the same time of the antigen-antibody reaction or after completion of the reaction, an excessive amount of the labeled primary antibody is further allowed to come into contact with the resultant. If the analytical target exists in the test sample, an immune complex of the immobilized second antibody, the analytical target (antigen) and the labeled primary antibody is formed.

In the sandwich method, after completion of the reaction of the immobilized primary antibody, the analytical target (antigen) and the secondary antibody, the labeled secondary antibody that has not formed the aforementioned immune complex is removed. Subsequently, a region of the insoluble thin-membrane support, on which the second antibody has been immobilized, may be observed so as to detect or quantify the labeling substance, and detect the presence or absence of the analyte in the test sample or measure the amount of the analyte. Alternatively, a metal ion and a reducing agent are supplied, so that a signal from the labeling substance of the labeled primary antibody that has formed the aforementioned immune complex may be amplified and detected. Otherwise, a metal ion and a reducing agent are added to the labeled primary antibody, and they are simultaneously added to the thin-membrane support, so that a signal from the labeling substance of the labeled secondary antibody that has formed the aforementioned immune complex may be amplified, detected and measured.

In the competitive method, an analytical target can be analyzed by the following procedures, for example, but the procedures are not particularly limited thereto. The competitive method is known as a means for detecting a low molecular weight antigen which can not be assayed in the sandwich method.

First, a primary antibody having specificity for an analytical target (an antigen) has previously been prepared. In addition, the primary antibody has previously been labeled with metal colloid or the like. An analytical target, or a compound which has a site which is similar with that of the analytical target and has a same epitope against the primary antibody as that of the analytical target, both of which can bind to the primary antibody, is immobilized on a suitable insoluble thin-membrane support (e.g. a nitrocellulose membrane, a glass fiber membrane, a nylon membrane, a cellulose membrane, etc.). It is then allowed to come into contact with a test sample (or an extract thereof) that is likely to contain the analytical target (the antigen). If the analytical target does not exist in the test sample, an antigen-antibody reaction occurs on the insoluble support between the labeled primary antibody, and the analytical target, or the compound which has a same epitope against the primary antibody as that of the analytical target, both of which can bind to the primary antibody. If the analytical target exists in the test sample, the analytical target (antigen) binds to the labeled primary antibody, and thus an antigen-antibody reaction on the insoluble support between the labeled primary antibody, and the analytical target, or the compound which has a same epitope against the primary antibody as that of the analytical target, both of which can bind to the primary antibody, is inhibited. Namely, binding by the antigen-antibody reaction does not occur.

After completion of the reaction of the immobilized substance which can bind to the primary antibody and the labeled primary antibody, the labeled primary antibody that has not formed the aforementioned immune complex is removed. Subsequently, the substance which can bind to the primary antibody on the insoluble carrier may be observed so as to detect or quantify the labeling substance, and detect the presence or absence of the analyte in the test sample or measure the amount of the analyte. Also, a metal ion and a reducing agent are supplied to a region of the insoluble thin-membrane support, on which the substance which can bind to the primary antibody has been immobilized, for example, so that a signal from the labeling substance of the labeled primary antibody which formed immune complex may be amplified and detected. Otherwise, a metal ion and a reducing agent are added to the labeled primary antibody, and they are simultaneously added to the thin-membrane support, so that a signal from the labeling substance of the labeled secondary antibody that has formed the aforementioned immune complex may be amplified, detected and measured.

6. Amplification Solution

An amplification solution that can be used in the present invention is what is called a developing solution as described in publications common in the field of photographic chemistry (e.g. "*Kaitei Shashin kagaku no kiso, Ginen shashin hen* (Revised Basic Photographic Engineering, silver salt photography)," (the Society of Photographic Science and Technology of Japan, Colona Publishing Co., Ltd.); "*Shashin no kagaku* (Photographic Chemistry)," (Akira Sasaki, Shashin Kogyo Shuppan); "*Saishin Shoho Handbook* (Latest Formulation Handbook)," (Shinichi Kikuchi et al., Amiko Shuppan); etc.).

In the present invention, any type of amplification solution can be used, as long as it is what is called a physical developing solution, which comprises silver ions, and such silver ions in the solution act as a core of development and reduction is carried out using a metal colloid as a center.

7. Compound that Contains Silver

The silver-containing compound used in the present invention may be an organic silver salt, an inorganic silver salt, or a silver complex.

The organic silver salt used in the present invention is an organic compound containing a reducible silver ion. Any one of an organic silver salt, an inorganic silver salt and a silver complex may be used as a compound containing a reducible silver ion in the present invention. For example, a silver nitrate, a silver acetate, a silver lactate, a silver butyrate, etc. have been known.

In addition, such a compound may be a silver salt or a coordination compound that forms a metallic silver relatively stable for light, when it is heated to 50° C. in the presence of a reducing agent.

The organic silver salt used in the present invention may be a compound selected from the silver salts of an azole compound and the silver salts of a mercapto compound. Such an azole compound is preferably a nitrogen-containing heterocyclic compound, and more preferably a triazole compound and a tetrazole compound. The mercapto compound is a compound having at least one mercapto group or thione group in the molecule thereof.

The silver salt of the nitrogen-containing heterocyclic compound of the present invention is preferably the silver salt of a compound having an imino group. Typical compounds include, but are not limited to, the silver salt of 1,2,4-triazole, the silver salt of benzotriazole or a derivative thereof (for example, a methylbenzotriazole silver salt and a 5-chlorobenzotriazole silver salt), a 1H-tetrazole compound such as phenylmercaptotetrazole described in U.S. Pat. No. 4,220,709, and imidazole or an imidazole derivative described in U.S. Pat. No. 4,260,677. Among these types of silver salts, a benzotriazole derivative silver salt or a mixture of two or more silver salts is particularly preferable.

The silver salt of the nitrogen-containing heterocyclic compound used in the present invention is most preferably the silver salt of a benzotrialzole derivative.

The compound having a mercapto group or a thione group of the present invention is preferably a heterocyclic compound having 5 or 6 atoms. In this case, at least one atom in the ring is a nitrogen atom, and other atoms are carbon, oxygen, or sulfur atoms. Examples of such a heterocyclic compound include triazoles, oxazoles, thiazoles, thiazolines, imidazoles, diazoles, pyridines, and triazines. However, examples are not limited thereto.

Typical examples of the silver salt of the compound having a mercapto group or a thione group include, but are not limited to, the silver salt of 3-mercapto-4-phenyl-1,2,4-triazole, the silver salt of 2-mercapto-benzimidazole, the silver salt of 2-mercapto-5-aminothiazole, the silver salt of mercaptotriazine, the silver salt of 2-mercaptobenzoxazole, and the silver salt of compounds described in U.S. Pat. No. 4,123, 274.

As such a compound having a mercapto group or a thione group of the present invention, a compound that does not contain a hetero ring may also be used. As such a mercapto or thione derivative that does not contain a hetero ring, an aliphatic or aromatic hydrocarbon compound having total 10 or more carbon atoms is preferable.

Among such mercapto or thione derivatives that do no contain a hetero ring, useful compounds include, but are not limited to, the silver salt of thioglycolic acid (for example, the silver salt of S-alkylthioglycolic acid having an alkyl group containing 12 to 22 carbon atoms) and the silver salt of dithiocarboxylic acid (for example, the silver salt of dithioacetic acid and the silver salt of thioamide).

An organic compound having the silver salt of carboxylic acid is also preferably used. It is straight-chain carboxylic acid, for example. Specifically, carboxylic acid containing 6 to 22 carbon atoms is preferably used. In addition, the silver salt of aromatic carboxylic acid is also preferable. Examples of such aromatic carboxylic acid and other carboxylic acids include, but are not limited to, substituted or unsubstituted silver benzoate (for example, silver 3,5-dihydroxybenzoate, silver o-methylbenzoate, silver m-methylbenzoate, silver p-methylbenzoate, silver 2,4-dichlorobenzoate, silver acetamide benzoate and silver p-phenylbenzoate), silver tannate, silver phthalate, silver terephthalate, silver salicylate, silver phenylacetate, and silver pyromellitate.

In the present invention, aliphatic acid silver containing a thioether group as described in U.S. Pat. No. 3,330,663 can also be preferably used. A soluble silver carboxylate having a hydrocarbon chain containing an ether bond or a thioether bond, or a soluble silver carboxylate having a sterically hindered substituent on an $\alpha$-position (of the hydrocarbon group) or an ortho-position (of the aromatic group) can also be used. These silver carboxylates have an improved solubility in a coating solvent, which provides a coating material having little light scattering.

Such silver carboxylates are described in U.S. Pat. No. 5,491,059. All of the mixtures of the silver salts described therein can be used in the invention, as necessary.

The silver salt of sulfonate as described in U.S. Pat. No. 4,504,575 can also be used in the embodiment of the present invention.

Further, for example, the silver salt of acetylene described in U.S. Pat. Nos. 4,761,361 and No. 4,775,613 can also be used in the present invention. It can be provided as a core-shell type silver salt as described in U.S. Pat. No. 6,355,408. Such silver salt is composed of a core consisting of one or more silver salts and a shell consisting of one or more different silver salts.

In the present invention, another product useful as a non-photosensitive silver source is a silver dimer composite consisting of two different types of silver salts described in U.S. Pat. No. 6,472,131. Such a non-photosensitive silver dimer composite consists of two different types of silver salts. When the aforementioned two types of silver salts include a linear saturated hydrocarbon group as a silver ligand, a difference in the numbers of carbon atoms of the ligands is 6 or greater.

The organic silver salt is contained as silver generally in an amount of 0.001 to 0.2 mol/m$^2$, and preferably 0.01 to 0.05 mol/m$^2$, in terms of the silver amount.

The inorganic silver salt or the silver complex used in the present invention is a compound containing a reducible silver ion. Preferably, such an inorganic silver salt or a silver complex is an inorganic silver salt or a silver complex, which forms metallic silver relatively stable for light, when the salt or complex is heated to 50° C. or higher in the presence of a reducing agent.

Examples of the inorganic silver salt used in the present invention include: a silver halide (such as silver chloride, silver bromide, silver chlorobromide, silver iodide, silver chloroiodide, silver chloroiodobromide, and silver iodobromide); the silver salt of a silver thiosulfate (e.g. a sodium salt, a potassium salt, an ammonium salt, etc.); the silver salt of a silver thiocyanate (e.g. a sodium salt, a potassium salt, an ammonium salt, etc.); and the silver salt of a silver sulfite (e.g. a sodium salt, a potassium salt, an ammonium salt, etc.).

The inorganic silver salt used in the present invention is preferably a silver halide or silver nitrate.

A method for forming the particles of the silver halide used in the invention is well known in the photographic industry. For example, methods described in Research Disclosure No. 17029, June 1978, and U.S. Pat. No. 3,700,458 may be used. Specifically, such a silver halide may be prepared by adding a silver-supplying compound (for example, a silver nitrate) and a halogen-supplying compound to a solution of a gelatin or other polymers.

The particle size of the silver halide is preferably very small in order to reduce examination noise. Specifically, the size is preferably 0.20 μm or less, more preferably 0.10 μm or less, and even more preferably in the range of nanoparticles. The term "particle size" is used herein to mean a diameter of a circular image having the same area as the projected area of the silver halide particle (the projected area of the main plane in the case of a tabular particle).

A silver thiosulfate, a silver thiocyanate, and a silver sulfite can also be prepared in the same manner as the formation of silver halide particles, by mixing a silver-supplying compound (such as a silver nitrate) with a thiosulfate (e.g. a sodium salt, a potassium salt, an ammonium salt, etc.), a thiocyanate (e.g. a sodium salt, a potassium salt, an ammonium salt, etc.), and a sulfite (e.g. a sodium salt, a potassium salt, an ammonium salt, etc.), respectively.

In general, if the concentration of silver ion in the amplification solution is too high, such silver ion is reduced in the amplification solution. In order to prevent such a phenomenon, a complexing agent may be used to cause the silver ion to form a complex. As such a complexing agent, amino acids such as glycine and histidine, heterocyclic bases, imidazole, benzimidazole, pyrazole, purine, pyridine, aminopyridine, nicotinamide, quinoline, and other similar aromatic heterocyclic compounds have been known. These compounds are described in E.P. Patent No. 0293947, for example. Further, as a complex salt-forming agent, thiosulfate, thiocyanate, and the like can also be used. Specific examples of the silver complex used in the present invention include a complex of a thiosulfate and a silver ion, a complex of a thiocyanate and a silver ion, a composite silver complex thereof, a complex of a sugar thione derivative and a silver ion, a complex of a cyclic imide compound (e.g. uracil, urazole, 5-methyluracil, barbituric acid, etc.) and a silver ion, and a complex of a 1,1-bissulfonylalkane and a silver ion. A preferred silver complex used in the invention is a complex of a cyclic imide compound (e.g. uracil, urazole, 5-methyluracil, barbituric acid, etc.) and a silver ion.

The silver complex used in the present invention may be prepared by a generally-known salt forming reaction. For example, the silver complex may be prepared by mixing in water or a water-miscible solvent a water-soluble silver supplier (such as a silver nitrate) with a ligand compound corresponding to the silver complex. The prepared silver complex can be used, after salts generated as by-products have been removed by a known desalting method such as dialysis or ultrafiltration.

The inorganic silver salt or the silver complex is contained as silver generally in an amount of 0.001 to 0.2 mol/m$^2$, and preferably 0.01 to 0.05 mol/m$^2$, in terms of the silver amount.

When an inorganic silver salt or a silver complex is used, a solvent for them is preferably used. The solvent used in the present invention is preferably a compound used as a ligand for forming a silver complex described in the above paragraphs for the "silver complex." Examples of such a compound used as a solvent in the present invention include a thiosulfate, a thiocyanate, a sugar thione derivative, a cyclic imide compound, and a 1,1-bissulfonylalkane. The solvent used in the present invention is more preferably a cyclic imide compound such as uracil, urazole, 5-methyluracil, or barbituric acid. The solvent used in the present invention is preferably used at a molar ratio of 0.1 to 10 moles with respect to silver ions.

8. Reducing Agent Used for Silver Ion

As a reducing agent used for silver ion, either inorganic or organic materials capable of reducing silver (I) ion to silver, or the mixtures thereof, may be used.

As an inorganic reducing agent, reducible metal salts and reducible metal complex salts whose valence can be changed with metal ions such as $Fe^{2+}$, $V^{2+}$ or $Ti^{3+}$ have been known. These salts can be used in the present invention. When such an inorganic reducing agent is used, it is necessary to form a complex with the oxidized ion or reduce it, so as to remove or detoxify the oxidized ion. For example, in a system using $Fe^{+2}$ as a reducing agent, citric acid or EDTA is used to form a complex with $Fe^{3+}$ as an oxide, so as to detoxify it.

In the present system, such an inorganic reducing agent is preferably used. The metal salt of $Fe^{2+}$ is more preferable.

Developing agents used for wet-process silver halide photographic-sensitized materials (for example, methyl gallate, hydroquinone, substituted hydroquinone, 3-pyrazolidones, p-aminophenols, p-phenylenediamines, hindered phenols, amidoximes, azines, catechols, pyrogallols, ascorbic acid (or derivatives thereof), and leuco dyes), or other materials known to those skilled in the art (see, for example, U.S. Pat. No. 6,020,117 (Bauer et al.)) may be used in the present invention.

The term "ascorbic acid reducing agent" means a complex of ascorbic acid and a derivative thereof. Ascorbic acid reducing agents are described in many publications, as described below, including, for example, U.S. Pat. No. 5,236,816 (Purol et al.) and publications cited therein.

The reducing agent used in the present invention is preferably an ascorbic acid reducing agent. Useful ascorbic acid reducing agents include ascorbic acid, an analogue thereof, an isomer thereof, and a derivative thereof. Examples of such compounds include the following compounds. However, examples are not limited thereto.

Examples of such compounds include D- or L-ascorbic acid and a sugar derivative thereof (for example, γ-lactoascorbic acid, glucoascorbic acid, fucoascorbic acid, glucoheptoascorbic acid, and maltoascorbic acid), sodium ascorbate, potassium ascorbate, isoascorbic acid (or L-erythroascorbic acid), and a salt thereof (for example, an alkali metal salt, an ammonium salt, or salts known in the art), and endiol-type ascorbic acid, enaminol-type ascorbic acid and thioenol-type ascorbic acid such as compounds described in U.S. Pat. No. 5,498,511, EP-A-0585,792, EP-A 0573700, EP-A 0588408, U.S. Pat. Nos. 5,089,819, 5,278,035, 5,384,232 and 5,376,510, JP 7-56286, U.S. Pat. No. 2,688,549, and Research Disclosure 37152 (March, 1995).

Among these compounds, D-, L-, and D,L-ascorbic acid (and an alkali metal salt thereof), and isoascorbic acid (and an alkali metal salt thereof) are preferable. Moreover, a sodium salt is a preferred salt thereof. If necessary, a mixture of these reducing agents may also be used.

A hindered phenol may be preferably used singly or in combination with one or more gradation-hardening reducing agents and/or contrast enhancers.

A hindered phenol is a compound having only one hydroxyl group on a benzene ring and also having at least one substituent at the ortho-position relative to the hydroxyl group. The hindered phenol reducing agent may have plural hydroxyl groups, as long as the hydroxyl groups are located on different benzene rings.

Examples of the hindered phenol reducing agent include binaphthols (that is, dihydroxybinaphthols), biphenols (that is, dihydroxybiphenols), bis(hydroxynaphthyl)methanes, bis(hydroxyphenyl)methanes (that is, bisphenols), hindered phenols, and hindered naphthols, each of which may be substituted.

Typical binaphthols include, but are not limited to 1,1'-bi-2-naphthol, 1,1'-bi-4-methyl-2-naphthol, and compounds described in U.S. Pat. Nos. 3,094,417 and 5,262,295.

Typical biphenols include, but are not limited to, 2-(2-hydroxy-3-t-butyl-5-methylphenyl)-4-methyl-6-n-hexylphenol, 4,4'-dihydroxy-3,3',5,5'-tetra-t-butylbiphenyl, 4,4'-dihydroxy-3,3',5,5'-tetramethylbiphenyl, and compounds described in U.S. Pat. No. 5,262,295.

Typical bis(hydroxynaphthyl)methanes include, but are not limited to, 4,4'-methylenebis(2-methyl-1-naphthol) and compounds described in U.S. Pat. No. 5,262,295.

Typical bis(hydroxyphenyl)methanes include, but are not limited to, bis(2-hydroxy-3-t-butyl-5-methylphenyl)methane (CAO-5), 1,1'-bis(2-hydroxy-3,5-dimethylphenyl)-3,5,5-trimethyl hexane (NONOX or PERMANAX WSO), 1,1'-bis(3,5-di-t-butyl-4-hydroxyphenyl)methane, 2,2'-bis(4-hydroxy-3-methylphenyl)propane, 4,4'-ethylidene-bis(2-t-butyl-6-methylphenol), 2,2'-isobutylidene-bis(4,6-dimethylphenol) (LOWINOX 221B46), 2,2'-bis(3,5-dimethyl-4-hydroxyphenyl)propane, and compounds described in U.S. Pat. No. 5,262,295.

Typical hindered phenols include, but are not limited to, 2,6-di-t-butylphenol, 2,6-di-t-butyl-4-methylphenol, 2,4-di-t-butylphenol, 2,6-dichlorophenol, 2,6-dimethylphenol, and 2-t-butyl-6-methylphenol.

Typical hindered naphthols include, but are not limited to, 1-naphthol, 4-methyl-1-naphthol, 4-methoxy-1-naphthol, 4-chloro-1-naphthol, 2-methyl-1-naphthol, and compounds described in U.S. Pat. No. 5,262,295.

Moreover, other compounds disclosed as reducing agents include amidoximes (for example, phenylamidoxime), 2-thienylamidoxime, p-phenoxyphenylamidoxime, a combination of an aliphatic carboxylic allyl hydrazide and ascorbic acid (for example, a combination of 2,2'-bis(hydroxymethyl)-propionyl-p-phenyl hydrazide and ascorbic acid), a combination of a polyhydroxybenzene and at least one of hydroxylamine, reductone and hydrazine (for example, a combination of hydroquinone and bis(ethoxyethyl)hydroxylamine), piperidi-4-methylphenylhydrazine, hydroxamic acids (for example, phenylhydroxamic acid, p-hydroxyphenylhydroxamic acid, and o-alaninehydroxamic acid), a combination of an azine and a sulfonamidophenol (for example, a combination of phenothiazine and 2,6-dichloro-4-benzenesulfonamidophenol), α-cyanophenylacetic acid derivatives (for example, ethyl-α-cyano-2-methylphenylacetic acid and ethyl-α-cyanophenylacetic acid), bis-o-naphthol (for example, 2,2'-dihydroxy-1-binaphthyl, 6,6'-dibromo-2,2'-dihydroxy-1,1'-binaphthyl, and bis(2-hydroxy-1-naphthyl)methane), a combination of bis-naphthol and a 1,3-dihydroxybenzene derivative (for example, 2,4-dihydroxybenzophenone and 2,4-dihydroxyacetophenone), 5-pyrazolones (for example, 3-methyl-1-phenyl-5-pyrazolone), reductones (for example, dimethylaminohexose reductone, anhydrodihydro-aminohexose reductone, and anhydrodihydro-piperidone-hexose reductone), indane-1,3-diones (for example, 2-phenylindane-1,3-dione), chromans (for example, 2,2-dimethyl-7-t-butyl-6-hydroxychroman), 1,4-dihydroxypyridines (for example, 2,6-dimethoxy-3,5-dicarbetoxy-1,4-dihydropyridine), ascorbic acid derivatives (1-ascorbic palmitate, ascorbic stearate), unsaturated aldehydes (ketones), and 3-pyrazolidones.

Examples of a reducing agent that can be used in the present invention include substituted hydrazines such as sulfonyl hydrazines described in U.S. Pat. No. 5,464,738. Other useful reducing agents are described, for example, in U.S. Pat. Nos. 3,074,809, 3,094,417, 3,080,254 and 3,887,417. Auxiliary reducing agents descried in U.S. Pat. No. 5,981,151 are also useful.

The reducing agent may be a combination of a hindered phenol reducing agent and a compound selected from various auxiliary reducing agents such as those mentioned below. In addition, a mixture of such a combined agent plus a contrast enhancer (that is, a mixture of the 3 components) is also useful. As such an auxiliary reducing agent, it is possible to use trityl hydrazide and formyl-phenyl hydrazide described in U.S. Pat. No. 5,496,695.

A contrast enhancer may be used in combination with the reducing agent. Useful contrast enhancers include, but are not limited to, hydroxylamines (including hydroxylamine and alkyl- and aryl-substituted derivatives thereof), alkanolamines and phthalic ammonium described in U.S. Pat. No. 5,545,505, hydroxamic acid compounds described in U.S. Pat. No. 5,545,507, N-acylhydrazine compounds described in U.S. Pat. No. 5,558,983, and hydrogen atom donor compounds described in U.S. Pat. No. 5,637,449.

Not all combinations of reducing agents and organic silver salts are equally effective. A preferred combination is a benzotriazole silver salt used as an organic silver salt, a substituted compound thereof or a mixture thereof, with an ascorbic acid reducing agent used as a reducing agent.

The reducing agent of the present invention may be contained in an amount of 1 mass % to 10 mass % (dry mass) based on the amount of silver in organic silver. When the reducing agent is added to a layer other than the layer containing the organic silver salt in a multilayer structure, the amount of the reducing agent is slightly higher, and it is desirably from approximately 2 mass % to approximately 15 mass %. An auxiliary reducing agent is contained in an amount of about 0.001 mass % to 1.5 mass % (dry weight).

9. Other Auxiliary Agents

Other auxiliary agents contained in the amplification solution may include a buffer, an antiseptic such as an antioxidant or an organic stabilizer, and a speed regulator. Examples of a buffer used herein include buffers comprising acetic acid, citric acid, sodium hydroxide, a salt thereof, or tris(hydroxymethyl)aminomethane, and other buffers used in ordinary chemical experiments. Using these buffers as appropriate, the pH of the amplification solution can be adjusted to the optimal pH.

10. Method for Calculation of an Average Particle Size at the Time of Detection

At the time of detection (after amplification), a test line is cut out, and The rear surface of a sample was applied to a sample support using a carbon paste and then subjected to carbon coating. The shape and the size are observed by a scanning electron microscope (SEM). For example, the surfaces of samples are observed under SEM (specifically, under FE-STEM S-5500 (manufactured by Hitachi High-Technologies Corporation)) using acceleration voltage of 10 KV and reflected electrons. Subsequently, 100 signal particles are selected, and the circle-equivalent diameter of projected area of particles are measured. Then, the average particle size is calculated and is defined as the average particle size at the time of detection.

The present invention will be more specifically described in the following examples. However, these examples are not intended to limit the scope of the present invention.

EXAMPLES

Example 1

1) Preparation for Immunochromatography
1-1) Preparation of Anti-hCG Antibody-Modified Gold Colloid (Labeling Substance for Detection)

1 mL of a 50 μg/mL anti-hCG monoclonal antibody (Anti-hCG 5008 SP-5, Medix Biochemica) solution was added to a gold colloidal solution having pH adjusted by addition of 1 mL of a 50 mM $KH_2PO_4$ buffer (pH 7.0) to 9 mL of a 50-nm diameter gold colloidal solution (EM.GC50, BBI), followed by agitation. The mixture was allowed to stand for 10 minutes, and then 550 μL of 1% polyethylene glycol (PEG Mw. 20000, Product No. 168-11285, Wako Pure Chemical Industries, Ltd.) aqueous solution was added to the mixture, followed by agitation. A 10% bovine serum albumin (BSA Fraction V, Product No. A-7906, SIGMA) aqueous solution (1.1 mL) was added to the resultant, followed by agitation. The solution was centrifuged at 8000×g at 4° C. for 30 minutes (himacCF16RX, Hitachi). The supernatant was removed so that approximately 1 mL of the solution remained. The gold colloids were dispersed again using an ultrasonic washing machine. Subsequently, the solution was then dispersed in 20 mL of a gold colloidal stock solution (20 mM Tris-HCl buffer (pH 8.2), 0.05% PEG (Mw.20000), 150 mM NaCl, 1% BSA, and 0.1% $NaN_3$) and then centrifuged again at 8000×g at 4° C. for 30 minutes. The supernatant was removed so that approximately 1 mL of the solution remained. The gold colloids were dispersed again using an ultrasonic washing machine, so that an antibody-modified gold colloid (50 nm) solution was obtained.

1-2) Preparation of Gold Colloidal Antibody Holding Pad

The antibody-modified gold colloid prepared in 1-1 above was diluted with water and a coating solution for a gold colloid (20 mM Tris-Hcl buffer (pH 8.2), 0.05% PEG (Mw: 20000), and 5% sucrose) to set the OD at 520 nm to 1.5. This solution was uniformly applied to glass fiber pads (Glass Fiber Conjugate Pad, Millipore) cut to the size of 8 mm×150 mm in an amount of 0.8 mL per pad. The pads were dried under reduced pressure overnight to obtain gold colloidal antibody holding pads.

1-3) Preparation of Antibody-Immobilized Membrane (Chromatographic Carrier)

An antibody-immobilized membrane was prepared in the following manner by immobilizing an antibody on a nitrocellulose membrane (HiFlow Plus HF240 with a plastic lining, Millipore) cut to the size of 25 mm×200 mm. The membrane, with one of its long sides facing downward, was coated with an anti-hCG monoclonal antibody (for immobilization) (Anti-Alpha subunit 6601 SPR-5, Medix Biochemica) solution prepared at a concentration of 0.5 mg/ml with the use of a coater of inkjet type (BioDot Ltd.). Specifically, the membrane was coated so that a linear portion thereof 8 mm above the lower edge was coated to have a width of approximately 1 mm. In a similar manner, the membrane was coated with a control anti-mouse IgG antibody (anti-mouse IgG (H+L), rabbit F(ab')2, Product No. 566-70621, Wako Pure Chemical Industries, Ltd.) solution prepared at a concentration of 0.5 mg/ml, so that a linear portion thereof 12 mm above the lower edge was coated. The coated membrane was dried at 50° C. for 30 minutes with a hot-air dryer. The membrane was immersed in 500 ml of a blocking solution (50 mM borate buffer (pH 8.5) containing 0.5 w % casein (milk-derived product, Product No. 030-01505, Wako Pure Chemical Industries, Ltd.)) in a vat and then allowed to stand therein for 30 minutes. Thereafter, the membrane was transferred to and immersed in 500 ml of a washing-stabilizing solution (0.5 w % sucrose, 0.05 w % sodium cholate, and 50 mM Tris-HCl (pH 7.5)) in a similar vat and then allowed to stand therein for 30 minutes. The membrane was removed from the solution and then dried overnight at room temperature to give an antibody-immobilized membrane.

1-4) Preparation of Immunochromatography Membrane and Kit

The antibody-immobilized membrane 3 prepared in 1-3 above was adhered to a back pressure-sensitive adhesive sheet 1 (ARcare9020, NIPPN TechnoCluster, Inc.). At this time, the membrane was used with the anti-hCG antibody line side (one of the long sides of the membrane) facing downward. The gold colloidal antibody holding pad 2 prepared in 1-2 above was adhered onto the antibody-immobilized membrane such that the pad 2 overlapped the lower portion of the antibody-immobilized membrane by approximately 2 mm. The sample addition pad 5 (glass fiber pad (Glass Fiber Conjugate Pad, Millipore) cut to the size of 18 mm×150 mm was adhered to the gold colloidal antibody holding pad such that the sample addition pad 5 overlapped the lower portion of the gold colloidal antibody holding pad by approximately 4 mm. Four (4) absorbent pads 4 (cellulose membrane cut to the size of 20 mm×150 mm (Cellulose Fiber Sample Pad, Millipore)) were adhered onto the antibody-immobilized membrane such that the absorbent pads 4 overlapped the upper portion of the antibody-immobilized membrane by approximately 5 mm. With the use of a guillotine cutter (CM4000, NIPPN TechnoCluster, Inc.), the thus overlapped and adhered members were cut in parallel to the short sides of the overlapped members at 5-mm intervals, whereby 5 mm×55 mm immunochromatographic strips were prepared. These strips were placed in a plastic case (NIPPN TechnoCluster, Inc.), so as to prepare an immunochromatography kit for testing.

2) Amplification Test hCG (recombinant hCG R-506 manufactured by Rohto Pharmaceutical Co., Ltd.) was dissolved in a PBS buffer containing 1 mass % BSA to prepare test hCG solutions with the concentrations (mol/L) described in Table 1.100 μL of the antigen solution was introduced dropwise onto the thus prepared immunochromatography kit. The kit was then allowed to stand for 10 minutes. Developing solutions A to H (100 μL each) with the following compositions were introduced dropwise again onto immunochromatography kits. Five (5) minutes later, the test line sites were observed. The test line sites were determined based on the following criteria:

++: Visually observable clearly
+: Visually observable, but light
±: Visual observation limit
−: Impossible to observe visually 3) Observation of Signal Shape and Method for Calculation of Average Particle Size The rear surface of a sample was applied to a sample support using a carbon paste and then subjected to carbon coating. The surfaces of samples were observed under SEM (specifically, under FE-STEM S-5500 (manufactured by Hitachi High-Technologies Corporation)) using acceleration voltage of 10 KV and reflected electrons. Subsequently, 100 signal particles were selected, the circle-equivalent diameter of projected area of particles were measured, and then average particle sizes were calculated. Table 1 shows the results.

4) Measurement of the Amount of Gold which is Present at the Test Line Area

The amount of gold which is present at the test line area was measured by HR-ICP-MS measurement (type number: Element XR, Thermo Fisher Scientific Co.), and the amount of gold which is present was calculated. Table 2 shows the results.

Developing solution A (the present invention)

Preparation of Developing Solution A-1

The following solution was agitated until dissolution.

| | |
|---|---:|
| 1 mol/L Fe(NO$_3$)$_3$/9H$_2$O aqueous solution | 40 mL |
| Citric acid | 10.5 g |
| nC$_{12}$H$_{25}$NH$_2$ | 100 mg |
| C$_9$H$_{19}$—C$_6$H$_4$—O—(CH$_2$CH$_2$O)$_{50}$H | 100 mg |
| H$_2$O | 325 g |

40 mL of 10% nitric acid was added to the solution. Furthermore, 11.76 g of FeSO$_4$(NH$_4$)$_2$SO$_4$.6H$_2$O was added to prepare a developing solution A-1.

Preparation of developing solution A-2

H$_2$O was added to 10 mL of a silver nitrate solution (containing 0.179 g of silver nitrate) to a volume of 100 mL.

Preparation of Developing Solution A 40 mL of the A-1 solution, 4.25 mL of the A-2 solution, and 4.25 mL of H$_2$O were mixed to prepare a developing solution A.

Developing Solution B (the Present Invention)

A developing solution B was prepared in the same manner as that used for the developing solution A, provided that 7.84 g of FeSO$_4$(NH$_4$)$_2$SO$_4$.6H$_2$O and 3.92 g of H$_2$O were added.

Developing Solution C (the Present Invention)

A developing solution C was prepared in the same manner as that used for the developing solution A, provided that 3.92 g of FeSO$_4$(NH$_4$)$_2$SO$_4$.6H$_2$O and 7.84 g of H$_2$O were added.

Developing Solution D (Comparative Example)

A developing solution D was prepared in the same manner as that used for the developing solution A, provided that FeSO$_4$(NH$_4$)$_2$SO$_4$.6H$_2$O was not added and 11.76 g of H$_2$O was added.

Developing Solution E (the Present Invention)

A developing solution E was prepared in the same manner as that used for the developing solution A, provided that 8.5 mL of the A-2 solution was used and H$_2$O was not used.

Developing Solution F (Comparative Example)

A developing solution F was prepared in the same manner as that used for the developing solution A, provided that 2.1 mL of the A-2 solution was used and 6.4 mL of $H_2O$ was used.

Developing Solution G (Comparative Example)

A developing solution G was prepared in the same manner as that used for the developing solution A, provided that 12.5 mL of the A-2 solution was used and $H_2O$ was not used.

Developing Solution H (Comparative Example)

A Silver Enhancing Kit (SEKB250); manufactured by British Biocell International) was used as a developing solution.

Developing Solution I (Comparative Example)

A photo microscope silver amplification kit SEKL15 (British Biocell International) was used as a developing solution.

Table 1 shows the results.

TABLE 1

| | Developing solution | | | | | | | | |
|---|---|---|---|---|---|---|---|---|---|
| | A | B | C | D | E | F | G | H | I |
| | Average particle size (μm) | | | | | | | | |
| | 8.2 | 6.0 | 3.4 | 0.05 | 17.2 | 0.9 | 21.4 | 0.2 | 0.35 |
| $9 \times 10^{-12}$ | + | + | + | ± | + | + | + | + | + |
| $9 \times 10^{-13}$ | + | + | + | − | + | ± | ± | ± | ± |
| $9 \times 10^{-14}$ | + | + | + | − | + | − | − | − | − |
| $9 \times 10^{-15}$ | + | + | − | − | + | − | − | − | − |
| $9 \times 10^{-16}$ | + | − | − | − | + | − | − | − | − |
| $9 \times 10^{-17}$ | − | − | − | − | + | − | − | − | − |

TABLE 2

| Concentration of hCH antigen | Gold amount at test line (/mm³) |
|---|---|
| $9 \times 10^{-12}$ | $1 \times 10^7$ |
| $9 \times 10^{-13}$ | $1 \times 10^6$ |
| $9 \times 10^{-14}$ | $1 \times 10^5$ |
| $9 \times 10^{-15}$ | $1 \times 10^4$ |
| $9 \times 10^{-16}$ | $1 \times 10^3$ |
| $9 \times 10^{-17}$ | $1 \times 10^2$ |

In the case of the developing solution G the test lines were observed not at 5 minutes after, but at 2 minutes after introducing dropwise the developing solution G. At 5 minutes after introduction, the whole membranes other than the test lines appeared black so that no test lines could be detected.

Example 2

Anti-influenza type A antibody and anti-influenza type B antibody were tested in place of anti-hCG antibody. As a result, as shown in Table 3, the obtained results were almost similar with the results of Example 1.

TABLE 3

| Gold Amount at test line | Developing solution | | | | | | | | |
|---|---|---|---|---|---|---|---|---|---|
| (/mm³) | A | B | C | D | E | F | G | H | I |
| $1 \times 10^7$ | + | + | + | ± | + | + | + | + | + |
| $1 \times 10^6$ | + | + | + | − | + | + | ± | ± | ± |
| $1 \times 10^5$ | + | + | + | − | + | − | − | − | − |
| $1 \times 10^4$ | + | + | − | − | + | − | − | − | − |
| $1 \times 10^3$ | + | − | − | − | + | − | − | − | − |
| $1 \times 10^2$ | − | − | − | − | ± | − | − | − | − |
| Average particle size (μm) | 8.3 | 6.2 | 3.4 | 0.05 | 17.5 | 0.9 | 22.1 | 0.20 | 0.36 |

Example 3

The samples of Examples 1 and 2 were measured using a concentration analyzer for immunochromatography ICA-1000 (Hamamatsu Photonics K.K.), and the difference (ΔOD) of absorbance between the background and the line area was obtained and evaluated. 5 mAbs or more was defined as visual observation limit and evaluation was performed. The visual observation limit concentrations are shown in Table 4 and 5. The obtained results were almost similar with the results of Examples 1 and 2.

TABLE 4

The visual observation limit concentration of sample of Example 1

| Visual observation limit concentration | Developing Solution | | | | | | | | |
|---|---|---|---|---|---|---|---|---|---|
| | A | B | C | D | E | F | G | H | I |
| Gold amount present in test line (/mm³) | $1 \times 10^3$ | $1 \times 10^4$ | $1 \times 10^5$ | $1 \times 10^7$ | $1 \times 10^2$ | $1 \times 10^6$ | $1 \times 10^6$ | $1 \times 10^6$ | $1 \times 10^6$ |

TABLE 5

The visual observation limit concentration of sample of Example 2

| Visual observation limit concentration | Developing Solution | | | | | | | | |
|---|---|---|---|---|---|---|---|---|---|
| | A | B | C | D | E | F | G | H | I |
| Gold amount present in test line (/mm³) | $1 \times 10^3$ | $1 \times 10^4$ | $1 \times 10^5$ | $1 \times 10^7$ | $1 \times 10^3$ | $1 \times 10^6$ | $1 \times 10^6$ | $1 \times 10^6$ | $1 \times 10^6$ |

The invention claimed is:

1. An immunochromatography method comprising:
   (i) developing an analyte and a labeling substance which is modified with a first binding substance against the analyte in a mixed state on a porous carrier;
   (ii) capturing the analyte and the labeling substance at a reaction site on the porous carrier having a second binding substance, wherein the second binding substance is capable of binding the analyte or of binding to the first binding substance and the second binding substance captures a complex formed by the analyte and the labeling substance;
   (iii) adding a silver-containing compound and a reducing agent for silver ions at the reaction site on the porous carrier and forming particles having an average particle size of 1 μm to 20 μm, wherein a particle core is formed by the complex of the analyte and the labeling substance and the reaction time for sensitization using the silver-containing compound and the reducing agent for silver ions is within 7 minutes; and
   (iv) detecting the analyte by detecting the particles formed in step (iii).

2. The immunochromatography method according to claim 1, wherein the reducing agent for silver ions is $Fe^{2+}$ and wherein the first binding substance is an antibody, and/or the second binding substance is an antibody.

3. The immunochromatography method according to claim 1, wherein the number of the labeling substance captured on a detection site is $1\times10^6/mm^3$ or less.

4. The immunochromatography method according to claim 1, wherein the labeling substance is a metal colloid.

5. The immunochromatography method according to claim 1, wherein the labeling substance is a gold colloid, a silver colloid, or a platinum colloid.

6. The immunochromatography method according to claim 1, wherein the reducing agent for silver ions is $Fe^{2+}$.

* * * * *